United States Patent [19]

Norcini et al.

[11] Patent Number: 5,760,285

[45] Date of Patent: Jun. 2, 1998

[54] PHOSPHONYLDIPEPTIDES USEFUL IN THE TREATMENT OF CARDIOVASCULAR DISEASES

[75] Inventors: Gabriele Norcini, Vizzola Ticino; Gabriele Morazzoni, Lainate; Francesco Santangelo, Milan, all of Italy

[73] Assignee: Zambon Group S.p.A., Vicenza, Italy

[21] Appl. No.: 702,701

[22] PCT Filed: Apr. 11, 1995

[86] PCT No.: PCT/EP95/01322

§ 371 Date: Sep. 13, 1996

§ 102(e) Date: Sep. 13, 1996

[87] PCT Pub. No.: WO95/28417

PCT Pub. Date: Oct. 26, 1995

[30] Foreign Application Priority Data

Apr. 14, 1994 [IT] Italy ................... MI94A0696

[51] Int. Cl.$^6$ .............. C07F 9/22; A01N 57/36
[52] U.S. Cl. .............. 562/10; 514/110
[58] Field of Search .............. 562/10; 514/110

[56] References Cited

U.S. PATENT DOCUMENTS

| | | | |
|---|---|---|---|
| 4,379,146 | 4/1983 | Karanewsky et al. | 424/177 |
| 4,432,972 | 2/1984 | Greenlee et al. | 424/177 |
| 5,151,414 | 9/1992 | Casagrande et al. | 514/114 |
| 5,451,608 | 9/1995 | Santangelo et al. | 514/674 |

FOREIGN PATENT DOCUMENTS 518299 12/1992 European Pat. Off. ..

OTHER PUBLICATIONS

Merz et al., "Free Energy Perturbation Simulations of the Inhibition of Thermolysin: Prediction of the Free Energy of Binding of a New Inhibitor", *J. Am. Chem. Soc.*, vol. 111, No. 15 (1989), pp. 5649–5658.

Mookhtiar, K.A. et al., "Phosphonamidate Inhibitors of Human Neutrophil Collagenase". *Biochemistry*, vol. 26, No. 7 (1987), pp. 1962–1965.

McMahon et al., "Phosphoramidon Blocks the Pressor Activity of Porcine Big Endothelin–1–(1–39) In Vivo and Conversion of Big Endothelin–1–(1–39), 2 Endothelin–1–(1–21) In Vitro", *Proceedings National Academy of Science*, vol. 88 (Feb. 1991), pp. 703–707.

Fukuroda, T. et al., "Inhibition of Biological Action of Big Endothelin–1 by Phosphoramidon", *Biochemical and Biophysical Research Communication*, vol. 172, No. 2 (Oct. 30, 1990), pp. 390–395.

Rich, H. David, "Peptidase Inhibitors" in *Comprehensive Medicinal Chemistry: The Rational Design, Mechanistic Study & Therapeutic Application of Chemical Compounds*, vol. 2 (Pergamon Press PLC), pp. 391–496 (not continuous), 1990.

Kam, C.M. et al., "Inhibition of Thermolysin and Carboxy Peptidase A Biphosphoramides", *Biochemistry*, vol. 18, No. 14 (1979), pp. 3032–3038.

Carey et al., "Reactions and Synthesis": Chapter 11 entitled Multistep Synthesis at pp. 539, 553. *Advanced Organic Chemistry*, Second Ed., Part B (New York Plenum Press), 1983.

*Primary Examiner*—Paul J. Killos
*Attorney, Agent, or Firm*—Nikaido Marmelstein Murray & Oram LLP

[57] ABSTRACT

Compounds of formula (II)

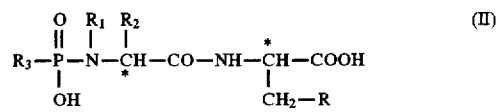

wherein R is a biphenyl group optionally substituted by one or more substituents, the same or different, selected among halogen atoms, hydroxy groups, alkoxy, alkyl or thioalkyl groups having from 1 to 6 carbon atoms in the alkyl moiety, carboxylic groups, nitro groups, amino, mono- or di-alkylamino groups having from 1 to 6 carbon atoms in the alkyl moiety; $R_1$ is a hydrogen atom or a straight or branched $C_1$–$C_4$ allyl; $R_2$ is a straight or branched $C_1$–$C_6$ alkyl or an arylalkyl having from 1 to 6 carbon atoms in the alkyl moiety wherein the aryl is a phenyl, a naphthyl or a 5 or 6 membered aromatic heterocycle with one or two heteroatoms selected among nitrogen, oxygen and sulphur, optionally substituted as above indicated for the R substituent; $R_3$ is a straight or branched $C_1$–$C_6$ alkyl, optionally containing one or more fluorine atoms, or an arylalkyl having from 1 to 6 carbon atoms in the alkyl moiety; the carbon atoms marked with an asterisk are asymmetric carbon atoms; and their pharmaceutically acceptable salts, are described. The compounds of formula (II) are useful in the treatment of cardiovascular diseases.

24 Claims, No Drawings

PHOSPHONYLDIPEPTIDES USEFUL IN THE TREATMENT OF CARDIOVASCULAR DISEASES

The present invention relates to some phosphonic acid derivatives useful in the treatment of cardiovascular diseases and, more particularly, it relates to some phosphonic acid derivatives useful in the treatment of cardiovascular diseases as metallopeptidase inhibitors.

The pharmacologic interest towards the study of metallopeptidase inhibitory molecules derives from the role that said enzymes exert on the level of the cardiocirculatory system.

It is well-known in fact that compounds with angiotensin converting enzyme (ACE) inhibitory activity are mainly useful as anti-hypertensives in that they inhibit the formation of angiotensin II, a substance which increases the blood pressure.

Compounds with endothelin converting enzyme (ECE) inhibitory activity are useful as anti-vasoconstrictors in that they inhibit the formation of endothelin, a 21 amino acid peptide with vasoconstrictor activity.

Instead, compounds with inhibitory activity of the neutral endopeptidase enzyme (NEP), also called enkephalinase, are useful as vasodilators in that the NEP enzyme is responsible for the inactivation, not only of endogenous enkephaline, but also of atrial natriuretic factor (ANF), a vasodilator hormone secreted by heart.

Therefore, even exerting their action on the cardiovascular system with different mechanisms of action, the compounds endowed with metallopeptidase inhibitory activity are generally used, alone or in combination, in the treatment of hypertension, renal failure and congestive heart failure.

The U.S. Pat. No. 4,432,972 (E. R. Squibb & Sons, Inc.) describes phosphonamidates which possess ACE-inhibitory activity and enkephalinase inhibitory activity useful as hypotensive and analgesic agents.

The European patent application No. 0518299 (Takeda Chemical Industries, Ltd.) describes compounds endowed with ECE-inhibitory activity useful in the treatment of hypertension, of cardiac or cerebral circulatory diseases and of renal diseases, having the general formula:

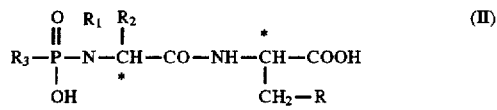

wherein $R_1$, $R_2$ and $R_3$ represent each a hydrocarbon radical which can be substituted, with the exception of the cases wherein (1) $R_2$ is an unsubstituted methyl, (2) $R_3$ is an unsubstituted hydrocarbon radical having from 1 to 3 carbon atoms, and (3) $R_1$ is benzyloxycarbonylaminomethyl, $R_2$ is isobutyl and $R_3$ is isobutyl or phenylmethyl.

Within the scope of the aforementioned patent application, the definition of optionally substituted hydrocarbon radical is extremely broad in that it comprises any radical formed from at least one to an infinite number of carbon atoms and optionally substituted by any other chemically compatible organic or inorganic group.

Among the meanings of optionally substituted hydrocarbon radical, alkyl, cycloalkyl and arylalkyl groups are specifically indicated. As a preferred arylalkyl group, in particular, an alkyl group having from 1 to 5 carbon atoms substituted by an aromatic hydrocarbon having from 6 to 12 carbon atoms, is intended; as a still more preferred arylalkyl group, a phenylmethyl group optionally substituted by lower alkyl or cycloalkyl groups, halogens, optionally protected hydroxy and alkoxy groups, is intended.

Now we have found that some of the compounds, which could be apparently considered comprised among the innumerable meanings for the substituents in the general formula I, but which were not specifically indicated in the combination of the meanings for $R_1$, $R_2$ and $R_3$, least of all exemplified in the European patent application No. 0518299, are endowed with a pharmacologic activity different from that described in the aforementioned European patent application and, in particular, are endowed with a mixed ACE-inhibitory and NEP-inhibitory activity.

This mixed inhibitory activity renders the compounds particularly useful in the cardiovascular therapy.

Therefore, object of the present invention are the compounds of formula

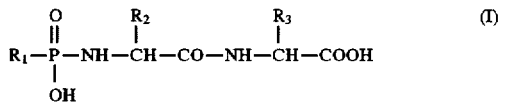

wherein

R is a biphenyl group optionally substituted by one or more substituents, the same or different, selected among halogen atoms, hydroxy groups, alkoxy, alkyl or thioalkyl groups having from 1 to 6 carbon atoms in the alkyl moiety, carboxylic groups, nitro groups, amino, mono- or di-alkylamino groups having from 1 to 6 carbon atoms in the alkyl moiety;

$R_1$ is a hydrogen atom or a straight or branched $C_1$–$C_4$ alkyl;

$R_2$ is a straight or branched $C_1$–$C_6$ alkyl or an arylalkyl having from 1 to 6 carbon atoms in the alkyl moiety wherein the aryl is a phenyl, a naphthyl or a 5 or 6 membered aromatic heterocycle with one or two heteroatoms selected among nitrogen, oxygen and sulphur, optionally substituted as above indicated for the R substituent;

$R_3$ is a straight or branched C–$C_6$ alkyl, optionally containing one or more fluorine atoms, or an arylalkyl having from 1 to 6 carbon atoms in the alkyl moiety; the carbon atoms marked with an asterisk are asymmetric carbon atoms;

and their pharmaceutically acceptable salts.

Object of the present invention are the compounds of formula II in the form of stereoisomeric mixture as well as in the form of single stereoisomers.

The compounds of formula II, object of the present invention, are endowed with mixed NEP-inhibitory and ACE-inhibitory activity and are useful in the treatment of cardiovascular diseases such as, for instance, hypertension, renal failure and congestive heart failure.

In the present description, unless otherwise specified, with the term biphenyl group we intend a 2-biphenyl, 3-biphenyl or 4-biphenyl group; with the term alkyl we intend a straight or branched alkyl such as methyl, ethyl, n.propyl, isopropyl, n.butyl, sec-butyl, tert-butyl, isobutyl, n.pentyl, 2-pentyl, 3-pentyl, isopentyl, tert-pentyl, n.hexyl and isohexyl; with the term halogen atom we intend a fluorine, chlorine, bromine or iodine atom; with the term aryl we intend an aromatic group such as phenyl, 1-naphthyl and 2-naphthyl or an aromatic heterocyclic group containing 1 or 2 heteroatoms selected among nitrogen, oxygen and sulphur such as thiazole, isoxazole, oxazole, isothiazole, pyrazole, imidazole, thiophene, pyrrole, pyridine, pyrimidine and furan, optionally benzocondensed.

Examples of pharmaceutically acceptable salts of the compounds of formula II are the salts with alkali or alkaliearth metals.

Preferred compounds of formula II are the compounds wherein R is an unsubstituted biphenyl group and, still more preferred are the compounds wherein said biphenyl group is a 4-biphenyl group.

A specific class of preferred compounds of formula II are the compounds wherein R is a 4-biphenyl group; $R_1$ is a hydrogen atom; $R_2$ is a straight or branched $C_3$–$C_6$ alkyl or an arylalkyl having from 1 to 3 carbon atoms in the alkyl moiety wherein the aryl is a phenyl, a naphthyl or a 5 or 6 membered aromatic heterocycle with one or two heteroatoms selected among nitrogen, oxygen and sulphur; $R_3$ is n.propyl or 2-phenylethyl.

Preferred examples of pharmaceutically acceptable salts of the compounds of formula II are the salts with alkali metals such as sodium, lithium and potassium.

Specific examples of preferred compounds of formula II, object of the present invention, are:

N-(N'-propylphosphonyl-L-leucyl)-(1,1'-biphenyl-4-yl)-L-alanine;

N-(N'-propylphosphonyl-L-phenylalanyl)-(1,1'-biphenyl-4-yl)-L-alanine;

N-(N'-propylphosphonyl-L-valyl)-(1,1'-biphenyl-4-yl)-L-alanine;

N-[N'-propylphosphonyl-(4-fluorophenyl)-L-alanyl]-(1,1'-biphenyl-4-yl)-L-alanine;

N-[N'-propylphosphonyl-(2-thienyl)-L-alanyl]-(1,1'-biphenyl-4-yl)-L-alanine;

N-[N'-propylphosphonyl-(2-naphthyl)-L-alanyl]-(1,1'-biphenyl-4-yl)-L-alanine;

N-[N'-propylphosphonyl-(1-naphthyl)-L-alanyl]-(1,1'-biphenyl-4-yl)-L-alanine;

N-[N'-propylphosphonyl-(4-thiazolyl)-L-alanyl]-(1,1'-biphenyl-4-yl)-L-alanine;

N-[N'-(2-phenyl)ethylphosphonyl-L-leucyl)-(1,1 1-biphenyl-4-yl)-L-alanine;

N-[N'-propylphosphonyl-(2-pyridyl)-L-alanyl]-(1,1'-biphenyl-4-yl)-L-alanine;

N-[N'-propylphosphonyl-(3-pyridyl)-L-alanyl]-(1,1'-biphenyl-4-yl)-L-alanine;

N-(N'-propylphosphonyl-L-tryptophyl)-(1,1'-biphenyl-4-yl)-L-alanine.

The preparation of the compounds of formula II, object of the present invention, comprises the reaction between a phosphorylated derivative of formula

(III)

wherein $R_3$ has the above reported meanings, X represents a halogen atom, preferably chlorine, and Y represents a protective group, preferably a $C_1$–$C_4$ alkyl, a phenyl or a phenylalkyl having from 1 to 4 carbon atoms in the alkyl moiety;

and a dipeptide derivative of formula

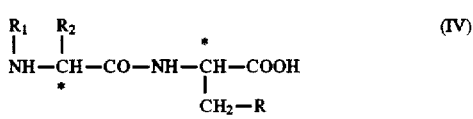

(IV)

wherein

R, $R_1$ and $R_2$ have the above reported meanings.

The phosphorylated derivative of formula III can be prepared from the corresponding compound of formula

(V)

wherein $R_3$ has the above reported meanings;

both Z contemporaneously represents a X or OY group wherein X and Y have the above reported meanings.

The preparation of the compound of formula III from the corresponding derivative of formula V is carried out, according to conventional techniques, by reaction with a halogenating agent or with a compound of formula YOH, wherein Y has the above reported meanings.

For a reference to the preparation of the compounds of formula III see, for instance, D. S. Karanewsky et al., J. Med. Chem. 1988, 31, 204–212.

The dipeptide derivatives of formula IV are prepared, in turn, through the condensation of an amino acid derivative of formula

(VI)

wherein $R_1$ and $R_2$ have the above reported meanings;

with a biphenylalanine derivative of formula

(VII)

wherein

R has the above reported meanings.

The condensation is carried out according to conventional techniques of the chemistry of peptides.

Before carrying out the reaction, it can be useful to properly protect the optional functional groups which could interfere in the reaction.

The optional protection is carried out according to conventional techniques.

For instance, in the reaction between the phosphorylated derivative of formula III and the dipeptide derivative of formula IV it can be useful to protect the free carboxylic function of the compound of formula IV as well as the free OH function of the phosphonic group.

Likewise, in the reaction between the amino acid derivative of formula VI and the biphenylalanine derivative of formula VII, it can be useful to protect the amino function of the derivative of formula VI and the carboxylic function of the derivative of formula VII.

Depending on the reaction to be carried out and on the functional groups to be protected, the evaluation of the usefulness of the optional protection as well as the selection of the kind of adopted protection, are within the normal knowledge of the man skilled in the art.

The removal of the optional protecting groups is carried out according to conventional techniques.

For a general reference to the use of protective groups in organic chemistry see Theodora W. Greene and Peter G. M. Wuts "Protective Groups in Organic Synthesis", John Wiley & Sons, Inc.

The compounds of formula VI and VII are known or easily prepared compounds according to known methods;

for a bibliographic reference to the preparation of biphenylalanine derivatives of formula VII see, for instance, Wen-Chung Shieh et al., J. Org. Chem. 1992, 57, 379–381.

The compounds of formula II in the form of single stereoisomers are prepared by stereoselective synthesis or by separation of the stereoisomeric mixture according to conventional techniques.

For instance, by using the amino acid derivatives of formula VI and VII with predetermined configuration as starting materials, the intermediates of formula IV and, thereafter, the corresponding compounds of formula II in the form of single stereoisomers will be obtained.

Also the preparation of the salts of the compounds of formula II, object of the invention, is carried out according to conventional techniques.

The compounds of formula II, object of the present invention, are endowed with mixed NEP-inhibitory and ACE-inhibitory activity and are useful in the treatment of cardiovascular diseases.

As compounds with mixed inhibitory activity we intend compounds which are endowed with an inhibitory activity substantially equipotent, that is to say active at the same concentrations, and pharmacologically significant on both NEP and ACE enzyme.

In this case only, in fact, it is possible the administration of a therapeutically effective dose of the active ingredient, namely, the administration of an amount of compound which contemporaneously and with equal strength elicits the inhibition of ACE and NEP enzyme.

The inhibitory activity of the compounds of formula II was evaluated by means of "in vitro" and "ex vivo" tests.

The "in vitro" inhibitory activity of the compounds of formula II, in particular, was evaluated in comparison to the compounds comprised in the aforementioned European patent application No. 0518299 and U.S. Pat. No. 4,432,972, as well as to known molecules with ACE-inhibitory or NEP-inhibitory activity (example 3).

Captopril, a drug known as the first orally active ACE-inhibitor (The Merck Index, XI Ed.—No. 1773, pages 267–268), was used as reference compound for the ACE-inhibitory activity.

Thiorphan [DL-(3-mercapto-2-benzylpropanoyl)glycine], known molecule considered the parent compound for NEP-inhibitors and described for the first time by Roques et al. in Nature, Vol. 288, pages 286–288, (1980), was used as reference compound for the NEP-inhibitory activity.

As further reference compounds, among those theoretically comprised in the European patent application No. 0518299, were taken into consideration those which, even not specifically described in said patent application, are structurally closest to the compounds of formula II, object of the present invention.

In particular, the compounds of formula II were compared with the compounds of formula I, comprised in the European patent application No. 0518299, wherein $R_3$ is a benzyl optionally substituted by halogen atoms or benzyloxy groups; said compounds are hereinafter referred to as the reference compounds R-1, R-2, R-3 and R-4.

Moreover, among the compounds structurally closest to the compounds of formula II, a reference compound explicitly described in the U.S. Pat. No. 4,432,972 was also taken into consideration; said compound is hereinafter referred to as reference compound R-5.

It is important to point out how the only structural difference between the compounds of formula II, object of the present invention, and the reference compounds is the presence of a biphenylmethyl group, in place of a benzyl, in α position to the C-terminal amino acid i.e. the replacement of phenylalanine residue with a biphenylalanine residue.

The "in vitro" inhibitory activity of the compounds of formula II resulted to be comparable to that of Captopril, as far as it concerns the ACE-inhibitory activity, and to that of thiorphan, as far as it concerns the NEP-inhibitory activity.

Nevertheless, the surprising aspect which characterizes the compounds of formula II, object of the present invention, is the fact that, unlike the compounds structurally closest among those described in the European patent application No. 0518299, they present a mixed inhibitory activity, that is to say a NEP-inhibitory as well as an ACE-inhibitory activity.

To this extent, it is worth noting that some of the reference compounds of formula I, even being endowed with a certain NEP-inhibitory activity, contemporaneously present an ACE-inhibitory activity at significantly higher and therapeutically useless doses.

Furthermore, the compounds of formula II resulted to be endowed with a mixed inhibitory activity on both ACE and NEP enzyme markedly higher with respect to the reference compound R-5, specifically described in the U.S. Pat. No. 4,432,972.

As previously pointed out, the inhibitory activity of the compounds of formula II was also evaluated by means of "ex vivo" tests (example 4).

The "ex vivo" NEP-inhibitory and ACE-inhibitory activity of the compounds of formula II was evaluated in comparison to a structurally related reference compound, in particular in comparison with the reference compound R-4, with is endowed with the best mixed inhibitory activity among the reference compounds tested in example 3.

It is worth noting, in this connection that said reference compound is comprised but not specifically described also in the aforementioned U.S. Pat. No. 4,432,972.

The "ex vivo" inhibitory activity of the compounds of formula II resulted to be significantly higher than that of the reference compound R-4 on both ACE and NEP enzyme.

So far, even if the reference compounds differ from the compounds of formula II by a chemical point of view only for the presence of a benzyl instead of a biphenylmethyl on the carbon a to the C-terminal amino acid, both the results from "in vitro" and "ex vivo" tests clearly demonstrate that the compounds of formula II are superior to the compounds described in the prior art.

These results are still more surprising if it is considered that they are due to the presence of a non-natural amino acid, i.e. a biphenylalanine, as an essential feature of the compounds object of the present invention. The essential requirement of a non-natural amino acid is not described or suggested in the prior art which, on the contrary, mainly relates to derivatives of natural amino acids.

The therapeutic advantage represented by a molecule having a significant mixed NEP-inhibitory and ACE-inhibitory activity is evident to the man skilled in the art.

It is well-known in fact that in the treatment of hypertension and of other cardiovascular pathologies it is generally useful, from a therapeutic point of view, to associate a compound with NEP-inhibitory activity with a compound with ACE-inhibitory activity [Pham I. et al., The Journal of Pharmacology and Experimental Therapeutics, vol. 263(3), pages 1339–47, (1993) and Seymour A. A. et al., Journal of Cardiovascular Pharmacology, vol. 17, pages 456–65, (1991)].

The mixed activity, therefore, allows an effective therapeutic treatment without the need of resorting to associations of more active ingredients.

It is important to point out that the use of a molecule with mixed activity represents an advantage also from the technological point of view in that it avoids formulative problems frequently related to the association of two or more active ingredients, not always compatible among them.

For a practical use in therapy the compounds of formula II can be formulated as solid or liquid pharmaceutical compositions, suitable to oral or parenteral administration.

The pharmaceutical compositions containing a therapeutically effective amount of a compound of formula II in admixture with a carrier for pharmaceutical use are, therefore, a further object of the present invention.

Specific examples of pharmaceutical compositions according to the present invention are tablets, coated tablets, capsules, granulates, solutions and suspensions suitable to oral administration, solutions and suspensions suitable to parenteral administration.

The pharmaceutical compositions object of the present invention are prepared according to conventional techniques.

The daily dose of the compound of formula II will depend on different factors such as the seriousness of the disease, the individual response of the patient or the kind of formulation but it is usually comprised between 0.1 mg and 50 mg per Kg of body weight divided into a single dose or into more daily doses.

Although the compounds of formula II are active as such, in order to satisfy specific therapeutic or pharmaceutical requirements, it can be useful to transform them into the corresponding biologic precursors (pro-drugs).

According to known techniques for the preparation of pro-drugs of phosphorylated derivatives and of dipeptide derivatives, suitable pro-drugs are obtained, for instance, through the esterification of the carboxylic groups or of the phosphonic groups.

The compounds of formula II even when transformed into pro-drugs and, in particular, the compounds obtained through the esterification of the carboxylic or phosphonic groups, as well as the pharmaceutical compositions which contain a compound of formula II in the form of the corresponding pro-drug and, in particular, which contain a compound of formula II wherein the carboxylic or phosphonic group has been esterified, are within the scope of the present invention.

With the aim of better illustrating the present invention the following examples are now given.

REFERENCE EXAMPLE 1

N-(N'-propylphosphonyl-L-leucyl)-(O-benzyl)-L-tyrosine dilithium salt (Compound R-1)

a) Preparation of N-(N'-tert-butoxycarbonyl-L-leucyl)-(O-benzyl)-L-tyrosine methyl ester Dicyclohexylcarbodiimide (10.3 g; 0.05 moles) was added to a solution of N-tert-butoxycarbonyl-L-leucine (5 g; 0.02 moles) and N-hydroxysuccinimide (2.55 g; 0.022 moles) in dioxane (50 ml), under nitrogen and under stirring at 0° C.

Two hours later, dicyclohexylurea was filtered off and (O-benzyl)-L-tyrosine methyl ester hydrochloride (7.6 g; 0.02 moles) and triethylamine (4.2 ml; 0.03 moles) were added to the resultant solution.

After three hours at room temperature, the reaction mixture was poured into water, extracted with ethyl acetate and the organic phase was dried on sodium sulphate.

The resultant crude from the evaporation of the solvent was column chromatographed (silica gel, eluent hexane:ethyl acetate=7:3) affording N-(N'-tert-butoxycarbonyl-L-leucyl)-(O-benzyl)-L-tyrosine methyl ester (5.7 g; 57% yield).

$^1$H-NMR (200 MHz, CDCl$_3$): δ(ppm): 0.90 (2d, 6H); 1.43 (s, 9H); 1.50–1.80 (m, 3H); 3.05 (dd, 2H); 3.68 (s, 3H); 4.06 (m, 1H); 4.78 (q, 1H); 5.00 (s, 2H); 6.86 (d, 2H); 7.00 (d, 2H); 7.20–7.45 (m, 5H).

b) Preparation of N-(L-leucyl)-(O-benzyl)-L-tyrosine methyl ester hydrochloride

Thionyl chloride (1.4 ml; 18.8 mmoles) was added dropwise to a solution of N-(N'-tert-butoxycarbonyl-L-leucyl)-(O-benzyl)-L-tyrosine methyl ester (4.7 g; 9 mmoles), prepared as described in point a), in methanol (30 ml).

After 4 hours at room temperature, the solvent was evaporated under vacuum and the residue was collected with toluene, obtaining a crystalline compound.

By filtration, N-(L-leucyl)-(O-benzyl)-L-tyrosine methyl ester hydrochloride (3.87 g; 99% yield) was obtained.

$^1$H-NMR (200 MHz, DMSO-d$_6$): δ (ppm): 0.89 (2d, 6H); 1.54 (t, 2H); 1.14 (m, 1H); 2.95 (dd, 2H); 3.58 (s, 3H); 3.77 (t, 1H); 4.57 (m, 1H); 5.05 (s, 2H); 6.92 (d, 2H); 7.16 (d, 2H); 7.25–7.50 (m, 5H).

c) Preparation of N-[N'-(phenoxy)(propyl)phosphoryl-L-leucyl]-(O-benzyl)-L-tyrosine methyl ester A solution of phenol (1.7 g; 0.018 moles) and triethylamine (2.5 ml; 0.018 moles) in methylene chloride (54 ml) was added dropwise, keeping the temperature below 0° C., to a solution of propylphosphonic dichloride (2.32 ml; 0.018 moles) in methylene chloride (54 ml), kept under nitrogen and under stirring.

After three hours at the same temperature, a solution of N-(L-leucyl)-(O-benzyl)-L-tyrosine methyl ester hydrochloride (4.5 g; 0.01 moles), prepared as described in point b), and triethylamine (3.9 ml; 0.028 moles) in methylene chloride (54 ml) was added dropwise at 0° C. and under nitrogen.

After one night at room temperature, the reaction mixture was poured into water.

The organic phase was separated, dried on sodium sulphate and evaporated to dryness.

The oily residue was column chromatographed (silica gel, eluent hexane:ethyl acetate=1:1) affording a solid which, washed with 60° C.–80° C. petroleum ether, furnished N-[N'-(phenoxy)(propyl)phosphoryl-L-leucyl]-(O-benzyl)-L-tyrosine methyl ester (1.8 g; 31% yield) as a white solid.

d) Preparation of N-(N'-propylphosphonyl-L-leucyl)-(O-benzyl)-L-tyrosine dilithium salt A solution of lithium hydroxide monohydrate (0.39 g; 9.3 mmoles) in water (10 ml) was added dropwise to a solution of N-[N'-(phenoxy)(propyl)phosphoryl-L-leucyl]-(O-benzyl)-L-tyrosine methyl ester (1.8 g; 3.1 mmoles), prepared as described in point c), in tetrahydrofuran (20 ml) under nitrogen.

After 24 hours at room temperature, the reaction mixture was diluted with water and washed with ethyl acetate.

The aqueous phase was concentrated under vacuum at small volume and was diluted with ethanol up to the formation of a precipitate which was filtered and dried under vacuum at 50° C.

N-(N'-propylphosphonyl-L-leucyl)-(O-benzyl)-L-tyrosine dilithium salt (1.34 g; 86% yield) was thus obtained as a whitish solid.

$^1$H-NMR (300 MHz, D$_2$O): δ (ppm): 0.70 (m, 9H); 1.03 (m, 2H); 1.23 (m, 2H); 1.40 (m, 1H); 2.71 (dd, 1H); 3.01 (dd, 1H); 3.33 (m, 1H); 4.25 (m, 1H); 4.27 (s, 2H); 6.82 (d, 2H); 7.02 (d, 2H); 7.30 (m, 5H).

REFERENCE EXAMPLE 2

N-(N'-propylphosphonyl-L-leucyl)-(3,4-dichlorophenyl)-L-alanine dilithium salt (Compound R-2)

a) Preparation of (3,4-dichlorophenyl)-L-alanine methyl ester hydrochloride

Thionyl chloride (0.478 ml; 6.58 mmoles) was added, under stirring and cooling into an ice-bath, to a solution of N-tert-butoxycarbonyl-(3,4-dichlorophenyl)-L-alanine (1.1 g; 3.29 mmoles) in methanol (20 ml).

After 24 hours at room temperature, the solvent was evaporated under vacuum affording a solid residue which, collected with ethyl ether, furnished (3,4-dichlorophenyl)-L-alanine methyl ester hydrochloride (910 mg; 97% yield) as a crystalline solid.

$^1$H-NMR (200 MHz, DMSO-$d_6$): δ (ppm): 3.16 (d, 2H); 4.70 (s, 3H); 4.35 (t, 1H); 7.25 (dd, 1H); 7.59 (dd, 2H).

b) Preparation of N-(N'-tert-butoxycarbonyl-L-leucyl)-(3,4-dichlorophenyl)-L-alanine methyl ester Dicyclohexylcarbodiimide (1.74 g; 8.45 mmoles) was added, under stirring and at room temperature, to a solution of N-tert-butoxycarbonyl-L-leucine monohydrate (957.3 mg; 3.84 mmoles) and N-hydroxysuccinimide (442 mg; 3.84 mmoles) in dioxane (20 ml).

After two hours, dicyclohexylurea was filtered off and (3,4-dichlorophenyl)-L-alanine methyl ester hydrochloride (910 mg; 3.2 mmoles), prepared as described in point a), and triethylamine (0.533 ml; 3.84 mmoles) were added to the resultant solution.

After 48 hours at room temperature, the reaction mixture was diluted with ethyl acetate, washed with water and dried on sodium sulphate.

The resultant crude from the evaporation of the solvent was column chromatographed (silica gel, eluent 60° C.–80° C. petroleum ether:ethyl acetate=7:3) affording a solid residue which, collected with petroleum ether, filtered and dried under vacuum at 40° C., furnished N-(N'-tert-butoxycarbonyl-L-leucyl)-(3,4-dichlorophenyl)-L-alanine methyl ester (1.15 g; 78% yield). m.p. 117°–119° C.

$^1$H-NMR (200 MHz, CDCl$_3$): δ (ppm): 0.91 (2d, 6H); 1.41 (s, 9H); 1.62 (m, 3H); 3.00 (dd, 1H); 3.14 (dd, 1H); 3.72 (s, 3H); 4.03 (m, 1H); 4.78 (q, 1H); 6.95 (dd, 1H); 7.20 (d, 1H); 7.33 (d, 1H).

c) Preparation of N-(L-leucyl)-(3,4-dichlorophenyl)-L-alanine methyl ester hydrochloride Thionyl chloride (0.356 ml; 4.9 mmoles) was added, under stirring and cooling into an ice-bath, to a solution of N-(N'-tert-butoxycarbonyl-L-leucyl)-(3,4-dichlorophenyl)-L-alanine methyl ester (1.13 g; 2.45 mmoles), prepared as described in point b), in methanol (20 ml).

After 5 hours under stirring at room temperature, the solvent was evaporated under vacuum affording an oily residue which, collected with ethyl ether, filtered and dried under vacuum at 40° C., furnished N-(L-leucyl)-(3,4-dichlorophenyl)-L-alanine methyl ester hydrochloride (940 mg; 96% yield) as a crystalline solid. m.p. 213°–214° C.

$^1$H-NMR (200 MHz, DMSO-$d_6$): δ (ppm): 0.87 (2d, 6H); 1.50 (t, 2H); 1.60 (m, 1H); 3.05 (m, 2H); 3.62 (s, 3H); 3.73 (t, 1H); 4.59 (m, 1H); 7.27 (dd, 1H); 7.55 (m, 2H).

d) Preparation of N-[N'-(phenoxy)(propyl)phosphoryl-L-leucyl]-(3,4-dichlorophenyl)-L-alanine methyl ester A solution of phenol (325.6 mg; 3.46 mmoles) and triethylamine (0.48 ml; 3.46 mmoles) in methylene chloride (5 ml) was added dropwise, keeping the temperature below 0° C., to a solution of propylphosphonic dichloride (0.432 ml; 3.46 mmoles) in methylene chloride (20 ml), kept under nitrogen and under stirring.

After three hours at room temperature, the reaction mixture was cooled at 0° C. and N-(L-leucyl)-(3,4-dichlorophenyl)-L-alanine methyl ester hydrochloride (920 mg; 2.31 mmoles), prepared as described in point c), and triethylamine (0.724 ml; 5.2 mmoles) were therein added under nitrogen.

After two hours at room temperature, the reaction mixture was diluted with methylene chloride, washed with water and dried on sodium sulphate.

After the evaporation to dryness of the solvent, the oily residue was column chromatographed (silica gel, eluent 60° C.–80° C. petroleum ether:ethyl acetate=1:1) affording a solid which, washed with petroleum ether, furnished N-[N'-(phenoxy)(propyl)phosphoryl-L-leucyl]-(3,4-dichlorophenyl)-L-alanine methyl ester (570 mg; 45% yield) as a white solid. m.p. 108°–115° C.

$^1$H-NMR (200 MHz, CDCl$_3$): δ (ppm): 0.80 (m, 6H); 1.00 (t, 3H); 1.20–2.00 (m, 7H); 2.72–3.20 (m, 2H); 3.17 (d, 3H); 3.80 (m, 1H); 4.68 (m, 1H); 6.80–7.35 (m, 8H).

e) Preparation of N-(N'-propylphosphonyl-L-leucyl)-(3,4-dichlorophenyl)-L-alanine dilithium salt A solution of lithium hydroxide monohydrate (127.14 mg; 3.03 mmoles) in water (5 ml) was added to a solution of N-[N'-(phenoxy)(propyl)phosphoryl-L-leucyl]-(3,4-dichlorophenyl)-L-alanine methyl ester (550 mg; 1.01 mmoles), prepared as described in point d), in tetrahydrofuran (10 ml) under nitrogen. After 3 hours at room temperature, the reaction mixture was diluted with water and washed twice with ethyl acetate.

The aqueous phase was concentrated under vacuum at small volume and was diluted with ethanol (100 ml) concentrating again at small volume with the formation of a precipitate.

Through the evaporation of the solvent, the resultant residue was collected with ethyl acetate, filtered and dried under vacuum at 50° C.

N-(N'-propylphosphonyl-L-leucyl)-(3,4-dichlorophenyl)-L-alanine dilithium salt (460 mg; 98% yield) was obtained as a whitish solid.

m.p. slow decomposition over 250° C. $^1$H-NMR (200 MHz, D$_2$O): δ (ppm): 0.72 (m, 9H); 1.00–1.50 (m, 7H); 2.72 (dd, 1H); 3.08 (dd, 1H); 3.34 (dd, 1H); 4.28 (dd, 1H); 7.00 (dd, 1H); 7.22 (bs, 1H); 7.30 (d, 1H). p Mass (chemical ionization, isobutane): 481 m/e (M+H$^+$ derived with CH$_2$N$_2$).

REFERENCE EXAMPLE 3

N-(N'-propylphosphonyl-L-leucyl)-(4-fluorophenyl)-L-alanine dilithium salt (Compound R-3)

a) Preparation of (4-fluorophenyl)-L-alanine methyl ester hydrochloride

Thionyl chloride (1.05 ml; 14.54 mmoles) was added, under stirring and cooling into an ice-bath, to a solution of N-tert-butoxycarbonyl-(4-fluorophenyl)-L-alanine (2.06 g; 7.27 mmoles) in methanol (40 ml).

After 24 hours at room temperature, the solvent was evaporated under vacuum affording a solid residue which, collected with ethyl ether, filtered and dried under vacuum at 40° C., furnished (4-fluorophenyl)-L-alanine methyl ester hydrochloride (1.64 g; 96% yield) as a crystalline solid.

m.p. 196°–197° C. $^1$H-NMR (200 MHz, DMSO-$d_6$): δ (ppm): 3.15 (t, 2H); 3.67 (s, 3H); 4.24 (t, 1H); 7.15 (t, 2H); 7.28 (dd, 2H).

b) Preparation of N-(N'-tert-butoxycarbonyl-L-leucyl)-(4-fluorophenyl)-L-alanine methyl ester Dicyclohexylcarbodiimide (4.24 g; 20.55 mmoles) was added, under stirring and at room temperature, to a solution of N-tert-butoxycarbonyl-L-leucine monohydrate (2.05 g; 8.22 mmoles) and N-hydroxysuccinimide (946 mg; 8.22 mmoles) in dioxane (40 ml).

After two hours, dicyclohexylurea was filtered off and (4-fluorophenyl)-L-alanine methyl ester hydrochloride (1.6 g; 6.85 mmoles), prepared as described in point a), and triethylamine (1.14 ml; 8.22 mmoles) were added to the resultant solution.

After 2.5 hours at 50° C. and 16 hours at room temperature, the reaction mixture was diluted with ethyl acetate, washed with water and dried on sodium sulphate.

The resultant crude from the evaporation of the solvent was column chromatographed (silica gel, eluent 60° C.–80° C. petroleum ether:ethyl acetate=7:3) affording a solid residue which, collected with petroleum ether, filtered and dried under vacuum at 40° C., furnished N-(N'-tert-butoxycarbonyl-L-leucyl)-(4-fluorophenyl)-L-alanine methyl ester (2.3 g; 82% yield).

m.p. 121°–122° C. $^1$H-NMR (200 MHz, CDCl$_3$): δ (ppm): 0.91 (2d, 6H); 1.41 (s, 9H); 1.60 (m, 3H); 3.08 (dd, 2H); 3.69 (s, 3H); 4.04 (m, 1H); 4.80 (q, 1H); 6.90–7.10 (m, 4H).

c) Preparation of N-(L-leucyl)-(4-fluorophenyl)-L-alanine methyl ester hydrochloride Thionyl chloride (0.8 ml; 10.96 mmoles) was added, under stirring and cooling into an ice-bath, to a solution of N-(N'-tert-butoxycarbonyl-L-leucyl)-(4-fluorophenyl)-L-alanine methyl ester (2.25 g; 5.48 mmoles), prepared as described in point b), in methanol (20 ml).

After 3 hours under stirring at room temperature, the solvent was evaporated under vacuum affording an oily residue which, collected with ethyl ether, filtered and dried under vacuum at 40° C., furnished N-(L-leucyl)-(4-fluorophenyl)-L-alanine methyl ester hydrochloride (1.79 g; 94% yield) as a crystalline solid.

m.p. 163°–164° C. $^1$H-NMR (200 MHz, DMSO-d$_6$): δ (ppm): 0.88 (2d, 6H); 1.54 (t, 2H); 1.63 (m, 1H); 3.02 (dd, 2H); 3.58 (s, 3H); 3.77 (s, 1H); 4.52 (m, 1H); 7.10 (t, 2H); 7.30 (dd, 2H).

d) Preparation of N-[N'-(phenoxy)(propyl)phosphoryl-L-leucyl]-(4-fluorophenyl)-L-alanine methyl ester A solution of phenol (712.4 mg; 7.57 mmoles) and triethylamine (1.05 ml; 7.57 mmoles) in methylene chloride (5 ml) was added dropwise, keeping the temperature below 0° C., to a solution of propylphosphonic dichloride (0.945 ml; 7.57 mmoles) in methylene chloride (50 ml), kept under nitrogen and under stirring.

After three hours at room temperature, the reaction mixture was cooled at 0° C. and N-(L-leucyl)-(4-fluorophenyl)-L-alanine methyl ester hydrochloride (1.75 g; 5.04 mmoles), prepared as described in point c), and triethylamine (1.58 ml; 11.34 mmoles) were therein added under nitrogen.

After two hours at room temperature, the reaction mixture was diluted with methylene chloride, washed with water and dried on sodium sulphate.

After the evaporation to dryness of the solvent, the oily residue was column chromatographed (silica gel, eluent 60° C.–80° C. petroleum ether:ethyl acetate=1:1) affording a solid which, washed with petroleum ether, furnished N-[N'-(phenoxy)(propyl)phosphoryl-L-leucyl]-(4-fluorophenyl)-L-alanine methyl ester (1.35 g; 54% yield) as a white solid.

m.p. 130°–140° C. $^1$H-NMR (200 MHz, CDCl$_3$): δ (ppm): 0.80 (m, 6H); 0.98 (bt, 3H); 1.20–1.95 (m, 7H); 3.00 (m, 2H); 3.65 (s, 3H); 3.80 (m, 1H); 4.70 (m, 1H); 6.80–7.38 (m, 9H).

e) Preparation of N-(N'-propylphosphonyl-L-leucyl)-(4-fluorophenyl)-L-alanine dilithium salt A solution of lithium hydroxide monohydrate (339.88 mg; 8.1 mmoles) in water (15 ml) was added to a solution of N-(N'-(phenoxy)(propyl)phosphoryl-L-leucyl]-(4-fluorophenyl)-L-alanine methyl ester (1.33 g; 2.7 mmoles), prepared as described in point d), in tetrahydrofuran (30 ml) under nitrogen.

After 3 hours at room temperature, the reaction mixture was reduced at small volume by evaporation under vacuum of most solvent, diluted with water and washed twice with ethyl acetate.

The aqueous phase was concentrated under vacuum at small volume and was diluted with ethanol (100 ml) concentrating again at small volume with the formation of a precipitate.

The precipitate was filtered, washed with ethanol and then with ether, and dried under vacuum at 50° C.

N-(N'-propylphosphonyl-L-leucyl)-(4-fluorophenyl)-L-alanine dilithium salt (670 mg; 60% yield) was obtained as a whitish solid.

m.p. higher than 300° C. $^1$H-NMR (200 MHz, D$_2$O): δ (ppm): 0.71 (m, 9H); 1.00–1.60 (m, 7H); 2.78 (dd, 1H); 3.02 (dd, 1H); 3.37 (m, 1H); 4.25 (dd, 1H); 6.90 (t, 2H); 7.07 (dd, 2H).

Mass (chemical ionization, isobutane): 431 m/e (M+H$^+$ derived with CH$_2$N$_2$).

REFERENCE EXAMPLE 4

N-(N'-propylphosphonyl-L-leucyl)-L-phenylalanine dilithium salt (Compound R-4)

a) Preparation of N-(N'-benzyloxycarbonyl-L-leucyl)-L-phenylalanine ethyl ester

A solution of dicyclohexylcarbodiimide (1.71 g; 8.3 mmoles) in dioxane (10 ml) was added, under stirring and under nitrogen at room temperature, to a solution of N-benzyloxycarbonyl-L-leucine (2 g; 7.55 mmoles) and N-hydroxysuccinimide (0.956 g; 8.3 mmoles) in dioxane (20 ml).

After one night, dicyclohexylurea was filtered off and L-phenylalanine ethyl ester (1.73 g; 7.55 mmoles) and triethylamine (1.05 ml; 7.55 mmoles) were added to the resultant solution.

After three hours at room temperature, the solvent was evaporated and the residue was diluted with water and extracted twice with ethyl acetate.

The organic phase was dried on sodium sulphate.

The resultant crude from the evaporation of the solvent was column chromatographed (silica gel, eluent 60° C.–80° C. petroleum ether:ethyl acetate=7:3) affording a solid residue which, collected with petroleum ether, filtered and dried under vacuum at 40° C., furnished N-(N'-benzyloxycarbonyl-L-leucyl)-L-phenylalanine ethyl ester (2.3 g; 69.3% yield).

$^1$H-NMR (200 MHz, CDCl$_3$): δ (ppm): 0.88 (d, 6H); 1.21 (t, 3H); 1.35–1.70 (m, 3H); 3.08 (dd, 2H); 4.14 (q, 2H); 4.80 (q, 1H); 5.08 (s, 2H); 5.09 (m, 1H); 7.00–7.40 (m, 10H).

b) Preparation of N-(L-leucyl)-L-phenylalanine ethyl ester hydrochloride

A solution of N-(N'-benzyloxycarbonyl-L-leucyl)-L-phenylalanine ethyl ester (2.3 g; 5.22 mmoles), prepared as described in point a), and hydrochloric acid 12N (0.435 ml; 5.22 mmoles) in ethanol (115 ml) was hydrogenated into a Parr apparatus at 3 atmospheres and at room temperature in the presence of palladium on charcoal at 10% (0.46 g).

After three hours, ended the hydrogen absorption, the catalyst was filtered off and the solution was evaporated under vacuum affording a residue which was crystallized from ethyl ether.

N-(L-leucyl)-L-phenylalanine ethyl ester hydrochloride (1.7 g; 95.5% yield) was obtained as a white solid.

$^1$H-NMR (200 MHz, DMSO-d$_6$): δ (ppm): 0.87 (2d, 6H); 1.09 (t, 3H); 1.54 (t, 2H); 1.66 (m, 1H); 3.02 (d, 2H); 3.78 (t, 1H); 4.02 (q, 2H); 4.50 (m, 1H); 7.26 (m, 5H).

c) Preparation of N-[N'-(phenoxy)(propyl)phosphoryl-L-leucyl]-L-phenylalanine ethyl ester A solution of phenol (0.414 g; 4.4 mmoles) and triethylamine (0.613 ml; 4.4 mmoles) in methylene chloride (10 ml) was added dropwise, keeping the temperature below 0° C., to a solution of propylphosphonic dichloride (0.708 g; 4.4 mmoles) in methylene chloride (10 ml), kept under nitrogen and under stirring.

After three hours at room temperature, the reaction mixture was cooled at 0° C. and a solution of N-(L-leucyl)-L-phenylalanine ethyl ester hydrochloride (1.0 g; 2.92 mmoles), prepared as described in point b), and triethylamine (1.02 ml; 7.3 mmoles) in methylene chloride (10 ml) was added dropwise under nitrogen.

After one night at room temperature, the reaction mixture was diluted with water and extracted with ethyl acetate.

The organic phase was dried on sodium sulphate and the solvent was evaporated under vacuum.

The oily residue was column chromatographed (silica gel, eluent 60° C.–80° C. petroleum ether:ethyl acetate=1:1) affording N-[N'-(phenoxy)(propyl)phosphoryl-L-leucyl]-L-phenylalanine ethyl ester (0.65 g; 46% yield) as a white solid.

$^1$H-NMR (200 MHz, CDCl$_3$): δ (ppm): 0.78 (m, 6H); 0.98 (t, 3H); 1.17 (t, 3H); 1.20–1.95 (m, 7H); 2.95 (d, 1H); 3.05 (dd, 1H); 3.78 (m, 1H); 4.10 (q, 2H); 4.72 (m, 1H); 7.00–7.35 (m, 10H).

d) Preparation of N-(N'-propylphosphonyl-L-leucyl)-L-phenylalanine dilithium salt A solution of lithium hydroxide monohydrate (0.168 g; 4 mmoles) in water (15 ml) was added dropwise to a solution of N-[N'-(phenoxy)(propyl)phosphoryl-L-leucyl]-L-phenylalanine ethyl ester (0.65 g; 1.33 mmoles), prepared as described in point c), in tetrahydrofuran (30 ml) under nitrogen.

After 36 hours at room temperature, the reaction mixture was reduced at small volume through the evaporation under vacuum of most solvent, diluted with water and washed twice with ethyl acetate.

The aqueous phase was concentrated under vacuum at small volume and was diluted with ethanol and with ether with the formation of a precipitate.

The precipitate was filtered affording N-(N'-propylphosphonyl-L-leucyl)-L-phenylalanine dilithium salt (0.46 g; 87.5% yield).

$^1$H-NMR (200 MHz, D$_2$O): δ (ppm): 0.70 (m, 9H); 0.95–1.05 (m, 7H); 2.77 (dd, 1H); 3.00 (dd, 1H); 3.32 (m, 1H); 4.24 (dd, 1H); 7.00–7.20 (m, 5H).

REFERENCE EXAMPLE 5

N-[N'-(4-phenyl)butylphosphonyl-L-phenylalanyl]-L-phenylalanine dilithium salt (Compound R-5)

The title compound was prepared according to the procedure described in the U.S. Pat. No. 4,432,972 (example 36).

Example 1

N-(N'-propylphosphonyl-L-leucyl)-(1,1'-biphenyl-4-yl)-L-alanine dilithium salt (Compound 1)

a) Preparation of (1,1'-biphenyl-4-yl)-L-alanine methyl ester hydrochloride

Thionyl chloride (0.81 ml; 11.12 mmoles) was added at room temperature to a solution of N-tert-butoxycarbonyl-(1,1-biphenyl-4-yl)-L-alanine (1.9 g; 5.56 mmoles) in methanol (40 ml).

After 24 hours, the reaction mixture was reduced at small volume by evaporation under vacuum obtaining a residue which, collected with ethyl ether, filtered and dried under vacuum at 40° C., furnished (1,1'-biphenyl-4-yl)-L-alanine methyl ester hydrochloride (1.6 g; 98% yield) as a crystalline solid.

m.p. 215°–216° C. $^1$H-NMR (200 MHz, DMSO-d$_6$): δ (ppm): 3.15 (dd, 2H); 3.70 (s, 3H); 4.30 (t, 1H); 7.25–7.52 (m, 5H); 7.65 (m, 4H).

b) Preparation of N-(N'-benzyloxycarbonyl-L-leucyl)-(1,1'-biphenyl-4-yl)-L-alanine methyl ester Dicyclohexylcarbodiimide (1.37 g; 6.6 mmoles) was added, under stirring and at room temperature, to a solution of N-benzyloxycarbonyl-L-leucine (1.6 g; 6 mmoles) and N-hydroxysuccinimide (0.69 g; 6 mmoles) in dioxane (32 ml).

After two hours, dicyclohexylurea was filtered off and (1,1'-biphenyl-4-yl)-L-alanine methyl ester hydrochloride (1.6 g; 5.48 mmoles), prepared as described in point a), and triethylamine (0.92 ml; 6.63 mmoles) were added to the resultant solution.

After heating at 60° C. for three hours, the reaction mixture was diluted with ethyl acetate, washed with water and dried on sodium sulphate.

The resultant crude from the evaporation of the solvent was column chromatographed (silica gel, eluent 60° C.–80° C. petroleum ether:ethyl acetate=60:40) obtaining a solid which, after washing with petroleum ether, furnished N-(N'-benzyloxycarbonyl-L-leucyl)-(1,1'-biphenyl-4-yl)-L-alanine methyl ester (2.1 g; 76% yield).

m.p. 126°–127° C. $^1$H-NMR (200 MHz, CDCl$_3$): δ (ppm): 0.90 (d, 6H); 1.35–1.75 (m, 3H); 3.15 (m, 2H); 3.74 (s, 3H); 4.15 (m, 1H); 4.87 (q, 1H); 5.07 (d, 2H); 7.05–7.60 (m, 14H).

c) Preparation of N-(L-leucyl)-(1,1'-biphenyl-4-yl)-L-alanine methyl ester hydrochloride A solution of N-(N'-benzyloxycarbonyl-L-leucyl)-(1,1'-biphenyl-4-yl)-L-alanine methyl ester (2.1 g; 4.18 mmoles), prepared as described in point b), and concentrated hydrochloric acid (0.35 ml) in ethanol (80 ml) was hydrogenated into a Parr apparatus at 3 atmospheres and at room temperature in the presence of palladium on charcoal at 10% (0.2 g).

After three hours, ended the hydrogen absorption, the catalyst was filtered off and the solution was evaporated under vacuum obtaining a residue which was crystallized from ethyl acetate.

N-(L-leucyl)-(1,1'-biphenyl-4-yl)-L-alanine methyl ester hydrochloride (1.47 g; 87% yield) was obtained as a white solid.

m.p. 185°–186° C. $^1$H-NMR (200 MHz, DMSO-d$_6$): δ (ppm): 0.90 (dd, 6H); 1.55 (t, 2H); 1.65 (m, 1H); 3.09 (m, 2H); 3.63 (s, 3H); 3.78 (t, 1H); 4.59 (q, 1H); 7.25–7.70 (m, 9H).

d) Preparation of N-[N'-(phenoxy)(propyl)phosphoryl-L-leucyl]-(1,1'-biphenyl-4-yl)-L-alanine methyl ester A solution of phenol (0.44 g; 4.63 mmoles) and triethylamine (0.64 ml; 4.63 mmoles) in methylene chloride (4.35 ml) was added dropwise, keeping the temperature below 0° C., to a solution of propylphosphonic dichloride (0.58 ml; 4.63 mmoles) in methylene chloride (30 ml), kept under nitrogen and under stirring.

After three hours at room temperature, the mixture was cooled at 0° C. and N-(L-leucyl)-(1,1'-biphenyl-4-yl)-L-alanine methyl ester hydrochloride (1.44 g; 3.56 mmoles), prepared as described in point c), and triethylamine (1.11 ml; 8.01 mmoles) were therein added.

After 16 hours at room temperature, the reaction mixture was diluted with methylene chloride, washed with water and dried on sodium sulphate.

After evaporation to dryness, the oily residue was column chromatographed (silica gel, eluent CH$_2$Cl$_2$:CH$_3$OH=98:2) obtaining a solid which, washed with ethyl ether:60° C.–80°

C. petroleum ether=1:3, furnished N-[N'-(phenoxy)(propyl) phosphoryl-L-leucyl]-(1,1'-biphenyl-4-yl)-L-alanine methyl ester (1.1 g; 56% yield) as a white solid.

m.p. 130° C. $^1$H-NMR (200 MHz, DMSO-d$_6$): δ (ppm): 0.55–0.90 (m, 9H); 1.10–1.70 (m, 7H); 2.96 (m, 2H); 3.60 (d, 3H); 3.68 (m, 1H); 4.48 (m, 1H); 7.00–7.70 (m, 14H).

e) Preparation of N-(N'-propylphosphonyl-L-leucyl)-(1,1'-biphenyl-4-yl)-L-alanine dilithium salt A solution of lithium hydroxide monohydrate (0.25 g; 6 mmoles) in water (7 ml) was added dropwise to a solution of N-[N'-(phenoxy)(propyl)phosphoryl-L-leucyl]-(1,1'-biphenyl-4-yl)-L-alanine methyl ester (1.1 g; 2 mmoles), prepared as described in point d), in tetrahydrofuran (30 ml).

After 72 hours at room temperature, the reaction mixture was diluted with water and washed with ethyl acetate.

The aqueous phase was concentrated under vacuum at small volume and diluted with ethanol up to the formation of a precipitate which was filtered and dried under vacuum at 50° C.

N-(N'-propylphosphonyl-L-leucyl)-(1,1'-biphenyl-4-yl)-L-alanine dilithium salt (0.77 g; 81% yield) was obtained as a whitish solid.

m.p. higher than 270° C. $^1$H-NMR (200 MHz, D$_2$O): δ (ppm): 0.65 (dd, 6H); 0.68 (t, 3H); 1.00–1.50 (m, 7H); 2.83 (dd, 1H); 3.14 (dd, 1H); 3.36 (m, 1H); 4.37 (dd, 1H); 7.15–7.60 (m, 9H).

Mass (chemical ionization, isobutane): 489 m/e (M+H$^+$ derived with CH$_2$N$_2$).

Example 2

N-(N'-propylphosphonyl-L-leucyl)-(4'-methoxy-1,1'-biphenyl-4-yl)-L-alanine dilithium salt (Compound 2)

a) Preparation of N-(N'-tert-butoxycarbonyl-L-leucyl)-(4'-methoxy-1,1'-biphenyl-4-yl)-L-alanine methyl ester Dicyclohexylcarbodiimide (7.3 g; 35 mmoles) was added to a solution of N-tert-butoxycarbonyl-L-leucine monohydrate (4.8 g; 19.2 mmoles) and N-hydroxysuccinimide (2.2 g; 19.2 mmoles) in dioxane (200 ml).

After one hour under stirring at room temperature, dicyclohexylurea was filtered off and a solution of (4'-methoxy-1,1'-biphenyl-4-yl)-L-alanine methyl ester hydrochloride (5 g; 16 mmoles) and triethylamine (2.7 ml; 19.2 mmoles) in dioxane (50 ml) was added to the resultant solution.

After 18 hours, the reaction mixture was evaporated under vacuum and the crude product was suspended in water and extracted with ethyl acetate.

The organic phase, separated and dried on sodium sulphate, was evaporated under vacuum affording a solid residue (10 g) which, purified by flash chromatography [flash chromatography silica gel (Baker—code 7024-00), eluent 40° C.–60° C. petroleum ether:ethyl acetate=75:25, pressure of nitrogen=0.2 atmospheres], furnished N-(N'-tert-butoxycarbonyl-L-leucyl)-(4'-methoxy-1,1'-biphenyl-4-yl)-L-alanine methyl ester (7 g; 88% yield) as a white solid.

$^1$H-NMR (200 MHz, CDCl$_3$): δ (ppm): 0.84–0.92 (m, 6H); 1.40 (s, 9H); 1.50–1.70 (m, 3H); 3.00–3.21 (m, 2H); 3.70 (s, 3H); 3.81 (s, 3H); 4.00–4.15 (m, 1H); 4.70–4.90 (m, 2H); 6.50 (d, 1H, NH); 6.90–7.50 (m, 8H).

b) Preparation of N-(L-leucyl)-(4'-methoxy-1,1'-biphenyl-4-yl)-L-alanine methyl ester hydrochloride Thionyl chloride (2.2 ml; 30.8 mmoles) was added at 0° C. to a solution of N-(N'-tert-butoxycarbonyl-L-leucyl)-(4'-methoxy-1,1'-biphenyl-4-yl)-L-alanine methyl ester (7 g; 14 mmoles), prepared as described in point a), in methanol (250 ml).

The reaction mixture was kept under stirring at room temperature for 24 hours.

At the end, the reaction mixture was evaporated under vacuum affording N-(L-leucyl)-(4'-methoxy-1,1'-biphenyl-4-yl)-L-alanine methyl ester hydrochloride (5.9 g; 97% yield) as a white solid.

$^1$H-NMR (200 MHz, CDCl$_3$): δ (ppm): 0.80–0.92 (m, 6H); 1.50–2.00 (m, 3H); 3.00–3.25 (m, 2H); 3.50 (s, 3H); 3.80 (s, 3H); 4.15–4.35 (m, 1H); 4.73–4.88 (m, 1H); 6.81–7.41 (m, 8H); 7.98 (d, 1H); 8.50 (bs, 3H).

c) Preparation of N-[N'-(phenoxy)(propyl)phosphoryl-L-leucyl]-(4'-methoxy-1,1'-biphenyl-4-yl)-L-alanine methyl ester A solution of phenol (0.81 g; 8.6 mmoles) and triethylamine (1.2 ml; 8.6 mmoles) in methylene chloride (10 ml) was added dropwise, under nitrogen and keeping the temperature at 0° C., to a solution of propylphosphonic dichloride (1.12 ml; 8.6 mmoles) in methylene chloride (25 ml).

After 3 hours under stirring at room temperature, the reaction mixture was cooled at 0° C. and a mixture of (L-leucyl)-(4'-methoxy-1,1'-biphenyl-4-yl)-L-alanine methyl ester hydrochloride (2.50 g; 5.75 mmoles), prepared as described in point b), and triethylamine (1.80 ml; 12.9 mmoles) in methylene chloride (20 ml) were added dropwise.

After 3 hours at room temperature, the reaction mixture was diluted with water and the phases were separated.

The organic phase was dried on sodium sulphate and evaporated to dryness under vacuum affording a residue which, purified by flash chromatography [flash chromatography silica gel (Baker—code 7024-00), eluent 40° C.–60° C. petroleum ether:ethyl acetate=1:1, pressure of nitrogen= 0.2 atmospheres], furnished N-[N'-(phenoxy)(propyl) phosphoryl-L-leucyl]-(4'-methoxy-1,1'-biphenyl-4-yl)-L-alanine methyl ester (1.5 g; 45% yield) as a white solid.

$^1$H-NMR (200 MHz, CDCl$_3$): δ (ppm): 0.70–0.85 (m, 6H); 0.90–1.90 (m, 10H); 3.65 (s, 3H); 2.90–3.80 (m, 4H); 3.81 (s, 3H); 4.70–4.82 (m, 1H); 6.62–6.85 (bs, 1H); 6.90–7.50 (m, 13H).

d) Preparation of N-(N'-propylphosphonyl-L-leucyl]-(4'-methoxy-1,1'-biphenyl-4-yl)-L-alanine dilithium salt A solution of lithium hydroxide monohydrate (0.3 g; 7.23 mmoles) in water (10 ml) was added to a solution of N-[N'-(phenoxy)(propyl)phosphoryl-L-leucyl]-(4'-methoxy-1,1'-biphenyl-4-yl)-L-alanine methyl ester (1.4 g; 2.41 mmoles), prepared as described in point c), in tetrahydrofuran (60 ml).

After one hour under stirring at room temperature, tetrahydrofuran was distilled off and the reaction mixture was diluted with water and washed twice with diethyl ether.

The aqueous phase was separated and evaporated to dryness under vacuum affording a solid which, collected with ethyl acetate, kept under stirring for 12 hours and filtered, furnished N-(N'-propylphosphonyl-L-leucyl)-(4'-methoxy-1,1'-biphenyl-4-yl)-L-alanine dilithium salt (0.52 g; 43% yield).

$^1$H-NMR (200 MHz, D$_2$O): δ (ppm): 0.55–0.69 (m, 9H); 1.00–1.49 (m, 7H); 3.25–3.37 (m, 1H); 3.66 (s, 3H); 4.28–4.35 (m, 1H); 6.85–7.45 (m, 8H).

By working as described in example 2, the following compounds were prepared:

N-(N'-propylphosphonyl-L-leucyl)-(1,1'-biphenyl-2-yl)-DL-alanine dilithium salt (Compound 3)

$^1$H-NMR (200 MHz, D$_2$O): δ (ppm): 0.59–0.72 (m, 9H); 0.93–1.45 (m, 7H); 2.64–3.34 (m, 3H); 3.98–4.10 (m, 1H); 7.06–7.40 (m, 9H).

N-(N'-propylphosphonyl-L-phenylalanyl)-(1,1'-biphenyl-4-yl)-L-alanine dilithium salt (Compound 4)

$^1$H-NMR (200 MHz, D$_2$O): δ (ppm): 0.51–0.58 (m, 3H); 0.85–1.08 (m, 4H); 2.54–2.73 (m, 2H); 3.60–3.71 (m, 1H); 4.26–4.33 (m, 1H); 6.93–7.50 (m, 14H).

N-(N'-propylphosphonyl-L-valyl)-(1,1'-biphenyl-4-yl)-L-alanine dilithium salt (Compound 5)

$^1$H-NMR (200 MHz, D$_2$O): δ (ppm): 0.41–0.63 (2d, 6H); 0.58–0.66 (m, 3H); 1.06–1.27 (m, 4H); 1.65–1.81 (m, 1H); 3.20 (dd, 1H); 4.27–4.34 (m, 1H); 7.17–7.51 (m, 9H).

N-(N'-propylphosphonyl-L-alanyl)-(1,1'-biphenyl-4-yl)-L-alanine dilithium salt (Compound 6)

$^1$H-NMR (200 MHz, D$_2$O): δ (ppm): 0.60–0.67 (m, 3H); 1.02 (t, 3H); 1.08–1.30 (m, 4H); 3.42 (dq, 1H); 4.24–4.31 (m, 1H); 7.55 (m, 9H).

N-(N'-propylphosphonyl-L-leucyl)-(4-methyl-1,1'-biphenyl-4-yl)-L-alanine dilithium salt (Compound 7)

$^1$H-NMR (200 MHz, D$_2$O): δ (ppm): 0.57–0.70 (m, 9H); 0.97–1.43 (m, 7H); 2.19 (s, 3H); 3.27–3.39 (m, 1H); 4.29–4.36 (m, 1H); 7.14–7.45 (m, 8H).

N-(N'-propylphosphonyl-L-leucyl)-(1,1'-biphenyl-3-yl)-DL-alanine dilithium salt (Compound 8)

$^1$H-NMR (200 MHz, D$_2$O): δ (ppm): 0.40–0.70 (m, 9H); 0.84–1.35 (m, 7H); 2.74–3.36 (m, 3H); 4.31–4.48 (m, 1H); 7.08–7.57 (m, 9H).

N-(N'-propylphosphonyl-L-leucyl)-(4'-chloro-1,1'-biphenyl-4-yl)-L-alanine dilithium salt (Compound 9)

$^1$H-NMR (200 MHz, D$_2$O): δ (ppm): 0.56–0.68 (m, 9H); 0.97–1.43 (m, 7H); 3.26–3.38 (m, 1H); 4.29–4.36 (m, 1H); 7.15–7.51 (m, 8H).

N-(N'-propylphosphonyl-L-leucyl)-(37-chloro-1,1'-biphenyl-4-yl)-L-alanine-dilithium salt (Compound 10)

$^1$H-NMR (200 MHz, D$_2$O+DMSO-d$_6$): δ (ppm): 0.55–0.69 (m, 9H); 0.93–1.40 (m, 7H); 2.71–3.15 (m, 2H); 3.25–3.34 (m, 1H); 4.27–4.33 (m, 1H); 7.15–7.51 (m, 8H).

N-[N'-propylphosphonyl-(4-fluorophenyl)-L-alanyl]-1,1'-biphenyl-4-yl)-L-alanine dilithium salt (Compound 11)

$^1$H-NMR (200 MHz, D$_2$O+DMSO-d$_6$): δ (ppm): 0.49–0.55 (m, 3H); 0.71–1.00 (m, 4H); 2.25–3.11 (m, 4H); 3.48–3.59 (m, 1H); 4.24–4.30 (m, 1H); 6.82–7.52 (m, 13H).

N-[N'-propylphosphonyl-(2-thienyl)-L-alanyl]-(1,1'-biphenyl-4-yl)-L-alanine dilithium salt (Compound 12)

$^1$H-NMR (200 MHz, D$_2$O): δ (ppm): 0.58–0.65 (m, 3H); 1.00–1.26 (m, 4H); 2.77–3.19 (m, 4H); 3.68–3.78 (m, 1H); 4.26–4.33 (m, 1H); 6.64–7.55 (m, 12H).

N-[N'-propylphosphonyl-(2-naphthyl)-L-alanyl]-(1,1'-biphenyl-4-yl)-L-alanine dilithium salt (Compound 13)

$^1$H-NMR (200 MHz, D$_2$O): δ (ppm): 0.30–0.36 (m, 3H); 0.72–1.02 (m, 4H); 2.73–2.95 (m, 4H); 3.72–3.82 (m, 1H); 4.26–4.32 (m, 1H); 6.63–7.62 (m, 16H).

N-[N'-propylphosphonyl-(1-naphthyl)-L-alanyl]-(1,1T-biphenyl-4-yl)-L-alanine dilithium salt (Compound 14)

$^1$H-NMR (200 MHz, D$_2$O): δ (ppm): 0.14–0.66 (m, 7H); 2.18–3.12 (m, 4H); 3.59–3.72 (m, 1H); 4.30–4.37 (m, 1H); 6.74–7.72 (m, 16H).

N-[N'-propylphosphonyl-(4-thiazolyl)-L-alanyl]-(1,1'-biphenyl-4-yl)-L-alanine dilithium salt (Compound 15)

$^1$H-NMR (200 MHz, D$_2$O): δ (ppm): 0.54–0.60 (m, 3H); 0.82–1.08 (m, 4H); 2.55–3.06 (m, 4H); 3.61–3.72 (m, 1H); 4.22–4.29 (m, 1H); 6.757 (d, 1H); 7.02–7.45.(m, 9H); 8.54 (d, 1H).

N-[N'-(2-phenyl)ethylphosphonyl-L-leucyl]-(1,1'-biphenyl-4-yl)-L-alanine dilithium salt (Compound 16)

$^1$H-NMR (200 MHz, D$_2$O+DMSO-d$_6$): δ (ppm): 0.63 (dd, 6H); 1.05 (m, 2H); 1.47 (m, 3H); 2.54 (m, 2H); 2.78 (dd, 1H); 3.10 (dd, 1H); 3.40 (m, 1H); 4.30 (dd, 1H); 7.00–7.50 (m, 14H).

N-[N'-propylphosphonyl-(2-pyridyl)-L-alanyl]-(1,1-biphenyl-4-yl)-L-alanine dilithium salt (Compound 17)

$^1$H-NMR (200 MHz, D$_2$O): δ (ppm): 0.48–0.55 (m, 3H); 0.70–1.03 (m, 4H); 2.44–3.08 (m, 4H); 3.65–3.76 (m, 1H); 4.23–4.30 (m, 1H); 6.89–7.51 (m, 12H); 8.15–8.19 (m, 1H).

N-[N'-propylphosphonyl-(3-pyridyl)-L-alanyl]-(1,1'-biphenyl-4-yl)-L-alanine dilithium salt (Compound 18)

$^1$H-NMR (200 MHz, D$_2$O): δ (ppm): 0.46–0.53 (m, 3H); 0.70–1.02 (m, 4H); 2.25–2.64 (m, 2H); 2.70–3.10 (m, 2H); 3.51–3.62 (m, 1H); 4.25–4.31 (m, 1H); 6.97–7.40 (m, 11H); 7.96–8.04 (m, 2H).

N-(N'-propylphosphonyl-L-tryptophyl)-(1,1'-biphenyl-4-yl)-L-alanine dilithium salt (Compound 19)

$^1$H-NMR (200 MHz, D$_2$O): δ (ppm): 0.40–0.46 (m, 3H); 0.76–1.03 (m, 4H); 2.51–2.79 (m, 2H); 2.81–3.06 (m, 2H); 3.70–3.80 (m, 1H); 4.19–4.25 (m, 1H); 6.42–7.50 (m, 14H).

Example 3

"In vitro" Evaluation of the Pharmacologic Activity a) NEP-inhibitory activity

The "in vitro" NEP-inhibitory activity was evaluated according to the method reported in the literature by C. Llorens et al., in Eur. J. Pharmacol., 69, (1981), 113–116.

Membranes from kidney cortex were prepared according to the following procedure.

Kidneys were removed from male Sprague-Dawley rats weighing approximately 300 g and were kept at 0°–4° C.

Cortex was carefully dissected, finely minced and suspended in a homogenization buffer (10 mM sodium phosphate pH 7.4 containing 1 mM MgCl$_2$, 30 mM NaCl, 0.02% NaN$_3$) 1:15 weight/volume.

The tissue was then homogenized for 30 seconds using an Ultra-Turrax homogenizer.

Approximately 10 ml of homogenate were layered over 10 ml of sucrose (41% weight/volume) and centrifuged at 31200 rpm for 30 minutes at 4° C. in a fixed angle rotor.

The membranes were collected from the buffer/sucrose interface, washed twice with 50 mM TRIS/HCl buffer (pH 7.4) and resuspended into the same buffer for storage.

The membranes were stored in small aliquots at −80° C. until use.

The NEP-inhibitory activity was evaluated by using the following method.

Aliquots of the membrane suspension prepared as above described (concentration 5 μg/ml of proteins) were preincubated in the presence of an aminopeptidase inhibitor (Bestatin-1 mM) for 10 minutes at 30° C.

[$^3$H][Leu$^5$]-enkephaline (15 nM) and buffer TRIS/HCl pH 7.4 (50 mm) were added in order to obtain a final volume of 100 μl.

Incubation (20 minutes at 30° C.) was stopped by adding HCl 0.1M (100 μl).

The formation of the metabolite [$^3$H]Tyr-Gly-Gly was quantified by chromatography on polystyrene columns containing Porapak Q resin. The inhibition of the metabolite formation in the membrane preparations treated with the compounds of formula II and the reference compounds, in comparison to the untreated membrane preparations, was expressed as IC$_{50}$ value (nM) or as percentage of inhibition.

b) ACE-inhibitory activity

The "in vitro" ACE-inhibitory activity was evaluated according to the method reported in the literature by B. Holmquist et al., in Analytical Biochemistry 95, 540–548 (1979).

50 μM of ACE (250 mU/ml purified by lung rabbit, EC 3.4.15.1 SIGMA) with 50 μl of the compound of formula II or of the reference compound were preincubated in thermostated cuvettes at 37° C. for 5 minutes.

The reaction was started by adding furylacryloylphenylalanylglycylglycine 0.8 mM (FAPGG-SIGMA).

Contemporaneously, by using a Beckman DU-50 spectrophotometer provided with a program for calculating delta A/minutes and regression coefficients of the enzyme kinetics curves, the absorbance at 340 nm was recorded in continuo for 5 minutes.

The percentage of enzyme inhibition in the preparations treated with the compounds of formula II and with the reference compounds with respect to the untreated preparations was expressed as $IC_{50}$ value (nM).

The inhibitory activity of the compounds of formula II, object of the present invention, was compared with the activity of the reference compounds R-1, R-2, R-3 and R-4 (European patent application No. 0518299), with the reference compound R-5 (U.S. Pat. No. 4,432,972), as well as with the NEP-inhibitory activity of thiorphan and with the ACE-inhibitory activity of Captopril.

The compounds of formula II and the reference compounds were tested in the form of lithium salts.

In the following table 1 we report the NEP-inhibitory and ACE-inhibitory activity of compound 1 in comparison to compound R-1, compound R-2, compound R-3, compound R-4, compound R-5, thiorphan and Captopril.

Table 1

"In vitro" NEP-inhibitory activity, expressed as $IC_{50}$ (nM) or as percentage of inhibition at a concentration corresponding to $_{10-8}$ M, and ACE-inhibitory activity, expressed as $IC_{50}$ (nM), of compound 1, compound R-1, compound R-2, compound R-3, compound R-4, compound R-5, thiorphan and Captopril.

| Compound | NEP-inhibitory activity | | ACE-inhibitory activity $IC_{50}$ (nM) |
|---|---|---|---|
| | $IC_{50}$ (nM) | % of inhibition ($10^{-8}$ M) | |
| 1 | 3.0 | 64 | 5.8 |
| R-1 | 139.0 | — | 13.3 |
| R-2 | 1.9 | — | 17.7 |
| R-3 | 5.41 | — | 35.1 |
| R-4 | 10.9 | — | 21.1 |
| R-5 | — | 42 | 20.0 |
| thiorphan | 11.3 | | 98.6 |
| Captopril | not active | | 2.8 |

The data reported in table 1 clearly show that only the compounds of formula II, object of the present invention, are endowed with a significant mixed NEP-inhibitory and ACE-inhibitory activity, so differing from the reference compounds.

The inhibitory activity of the compounds of formula II is, moreover, comparable to the ACE-inhibitory activity of Captopril as well as to the NEP-inhibitory activity of thiorphan.

Example 4
"Ex vivo" Evaluation of the Pharmacologic activity
a) NEP-inhibitory activity The "ex vivo" NEP-inhibitory activity was evaluated according to the procedure reported in the literature by M. Orlowsky et al., in Biochemistry 1981, 20, 4942–4950.

The inhibitory activity of the compounds of formula II or of the reference compound was evaluated in kidneys of spontaneously hypertensive rats (SHR), 5 minutes after i.v. injection of the tested compounds (21 μmoles/Kg).

After the removal of the kidneys from SHR, the renal tissue was homogenized and incubated for 15 minutes at 37° C. in the presence of Glutaryl-Ala-Ala-Phe-2-naphthylamide (GAAP), as a substrate, and aminopeptidase M at pH 7.6.

The reaction was stopped by adding an aqueous solution at 10% of trichloroacetic acid.

The released 2-naphthylamine was determined by adding fast garnet dye (2 ml).

Enzyme reaction rates were determined by measuring the increase in the optical density at 524 nm ($OD_{524}$) with respect to a standard obtained with 2-naphthylamine completed with fast garnet.

The NEP-inhibitory activity of the compounds of formula II and of the reference compound R-4 was expressed as percentage of NEP-inhibition in SHR kidneys.
b) ACE-inhibitory activity The "ex vivo" ACE-inhibitory activity was evaluated by using a radiometric assay method, as reported in the literature by J. W. Ryan et al. in Biochem. J. (1977), 167, 501–504.

The inhibitory activity of the compounds of formula II or of the reference compound was evaluated in lungs of spontaneously hypertensive rats (SHR), 5 minutes after i.v. injection of the tested compounds (21 μmoles/Kg).

After the removal of the lungs from SHR, the lung tissue was homogenized and incubated for 2 hours at 37° C. in the presence of [$^{3}$H]Hyp-Gly-Gly, as a substrate.

The reaction was stopped by adding hydrochloric acid.

The released radiolabelled hyppuric acid was extracted with ethyl acetate and counted by liquid scintillation spectrometry, according to conventional methods.

The ACE-inhibitory activity of the compounds of formula II and of the reference compound R-4 was expressed as percentage of ACE-inhibition in SHR lungs.

We report in the following table 2 the percentage of NEP-inhibition and ACE-inhibition, respectively evaluated in kidneys and lungs of SHR, of compound 1, compound 4, compound 5 and compound 8 in comparison to compound R-4.

Table 2

Percentage of "ex vivo" NEP-inhibition and ACE-inhibition of compound 1, compound 4, compound 5, compound 8 and compound R-4.

| Compound | NEP-inhibitory activity (kidney) % of inhibition | ACE-inhibitory activity (lung) % of inhibition |
|---|---|---|
| 1 | 74 ± 15 | 93 ± 8 |
| A | 61 ± A | 88 ± 3 |
| 5 | 73 ± 3 | 94 ± 3 |
| 8 | 75 ± 8 | 83 ± 3 |
| R-4 | 42 ± 6 | 65 ± 15 |

The data reported in table 2 clearly show that the compounds of formula II, object of the present invention, are endowed with a mixed NEP-inhibitory and ACE-inhibitory activity significantly higher than that of the reference compound R-4.

We claim:
1. A compound of formula

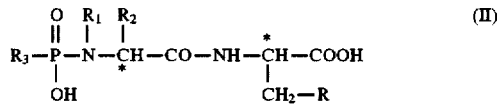

wherein

R is a biphenyl group optionally substituted by one or more substituents, the same or different, selected from the group consisting of halogen atoms, hydroxy groups, alkoxy, alkyl or thioalkyl groups having from 1 to 6 carbon atoms in the alkyl moiety, carboxylic groups, nitro groups, amino, and mono- or di-alkylamino groups having from 1 to 6 carbon atoms in the alkyl moiety;

21

$R_1$ is a hydrogen atom or a straight or branched $C_1$–$C_4$ alkyl;

$R_2$ is a straight or branched $C_1$–$C_6$ alkyl or an arylalkyl having from 1 to 6 carbon atoms in the alkyl moiety wherein the aryl is a phenyl, a napthyl or a 5 or 6 membered aromatic heterocycle with one or two heteroatoms selected from the group consisting of nitrogen, oxygen, and sulphur, optionally substituted as above indicated for the R substituent;

$R_3$ is a straight or branched $C_1$–$C_6$ alkyl, optionally containing one or more fluorine atoms, or an arylalkyl having from 1 to 6 carbon atoms in the alkyl moiety;

the carbon atoms marked with an asterisk are asymmetric carbon atoms;

and pharmaceutically acceptable salts thereof.

2. A compound according to claim 1 wherein R is an unsubstituted biphenyl group.

3. A compound according to claim 2 wherein R is a 4-biphenyl group.

4. A compound according to claim 1, 2 or 3 wherein R is a 4-biphenyl group; $R_1$ is a hydrogen atom; $R_2$ is a straight or branched $C_3$–$C_6$ alkyl or an arylalkyl having from 1 to 3 carbon atoms in the alkyl moiety wherein the aryl is a phenyl, a naphthyl or a 5 or 6 membered aromatic heterocycle with one or two heteroatoms selected among nitrogen, oxygen and sulphur; $R_3$ is n.propyl or 2-phenylethyl.

5. A compound according to claim 1 in the form of a salt with an alkali metal selected from the group consisting of sodium, lithium and potassium.

6. A pharmaceutical composition containing a therapeutically effective amount of a compound of formula II $$\begin{array}{c} O \quad R_1 \quad R_2 \\ \parallel \quad | \quad | \quad * \\ R_3-P-N-CH-CO-NH-CH-COOH \\ | \quad * \quad | \\ OH \quad CH_2-R \end{array} \quad (II)$$

wherein

R is a biphenyl group optionally substituted by one or more substituents, the same or different, selected from the group consisting of halogen atoms, hydroxy groups, alkoxy, alkyl or thioalyl groups having from 1 to 6 carbon atoms in the alkyl moiety, carboxylic groups, nitro groups, amino, and mono- or di-alkylamino groups having from 1 to 6 carbon atoms in the alkyl moiety;

$R_1$ is a hydrogen atom or a straight or branched $C_1$–$C_4$ alkyl;

$R_2$ is a straight or branched $C_1$–$C_6$ alkyl or an arylalkyl having from 1 to 6 carbon atoms in the alkyl moiety wherein the aryl is a phenyl, a napthyl or a 5 or 6 membered aromatic heterocycle with one or two heteroatoms selected from the group consisting of nitrogen, oxygen, and sulphur, optionally substituted as above indicated for the R substituent;

$R_3$ is a straight or branched $C_1$–$C_6$ alkyl optionally containing one or more fluorine atoms, or an arylalkyl having from 1 to 6 carbon atoms in the alkyl moiety;

the carbon atoms marked with an asterisk are asymmetric carbon atoms; in admixture with a carrier for pharmaceutical use.

7. A pharmaceutical composition according to claim 6 for the treatment of cardiovascular diseases.

8. N-(N'-propylphosphonyl-L-leucyl)-(1,1'-biphenyl-4-yl)-L-alanine according to claim 1.

9. N-(N'-propylphosphonyl-L-phenylalanyl)-(1,1'-biphenyl-4-yl)-L-alanine according to claim 1.

10. N-(N'-propylphosphonyl-L-valyl)-(1,1'-biphenyl-4-yl)-L-alanine according to claim 1.

11. N-(N'-propylphosphonyl-L-leucyl)-(1,1'-biphenyl-3-yl)-DL-alanine according to claim 1.

12. N-[N'-propylphosphonyl-(4-fluorophenyl)-L-alanyl]-(1,1'-biphenyl-4-yl)-L-alanine according to claim 1.

13. N-[N'-propylphosphonyl-(2-thienyl)-L-alanyl]-(1,1'-biphenyl-4-yl)-L-alanine according to claim 1.

14. N-[N'-propylphosphonyl-(2-naphthyl)-L-alanyl]-(1,1'-biphenyl-4-yl)-L-alanine according to claim 1.

15. N-[N'-propylphosphonyl-(1-naphthyl)-L-alanyl-]-(1,1'-biphenyl-4-yl)-L-alanine according to claim 1.

16. N-[N'-propylphosphonyl-(4-thiazolyl)-L-alanyl-]-(1,1'-biphenyl-4-yl)-L-alanine according to claim 1.

17. N-[N'-(2-phenyl) ethylphosphonyl-L-leucyl]-(1,1'-biphenyl-4-yl)-L-alanine according to claim 1.

18. N-[N'-propylphosphonyl-(2-pyridyl)-L-alanyl]-(1,1'-biphenyl-4-yl)-L-alanine according to claim 1.

19. N-[N'-propylphosphonyl-(3-pyridyl)-L-alanyl]-(1,1'-biphenyl-4-yl)-L-alanine according to claim 1.

20. N-(N'-propylphosphonyl-L-tryptophyl)-(1,1'-biphenyl-4-yl)-L-alanine according to claim 1.

21. N-(N'-propylphosphonyl-L-leucyl)-(4'-methoxy-1,1'-biphenyl-4-yl)-L-alanine according to claim 1.

22. N-(N'-propylphosphonyl-L-leucyl)-(4'-chloro-1,1'-biphenyl-4-yl)-L-alanine according to claim 1.

23. N-(N'-propylphosphonyl-L-leucyl)-(3'-chloro-1,1'-biphenyl-4-yl)-L-alanine according to claim 1.

24. A pharmaceutically acceptable salt of a compound according to any one of claims 8 to 23.

* * * * *

UNITED STATES PATENT AND TRADEMARK OFFICE
CERTIFICATE OF CORRECTION

PATENT NO. : 5,760,285

DATED : June 2, 1998

INVENTOR(S) : Norcini et al.

It is certified that error appears in the above-identified patent and that said Letters Patent is hereby corrected as shown below:

```
Item [30], delete "MI94A0696" insert therefor -- MI94A000696

--
```

Signed and Sealed this

Eleventh Day of August 1998

Attest:

BRUCE LEHMAN

*Attesting Officer*     *Commissioner of Patents and Trademarks*